(12) United States Patent
Slayton et al.

(10) Patent No.: US 11,097,133 B2
(45) Date of Patent: *Aug. 24, 2021

(54) METHOD AND SYSTEM FOR COMBINED ENERGY THERAPY PROFILE

(71) Applicant: Guided Therapy Systems, LLC, Mesa, AZ (US)

(72) Inventors: Michael H. Slayton, Tempe, AZ (US); Peter G. Barthe, Phoenix, AZ (US)

(73) Assignee: Guided Therapy Systems, LLC, Scottsdale, AZ (US)

( * ) Notice: Subject to any disclaimer, the term of this patent is extended or adjusted under 35 U.S.C. 154(b) by 521 days.

This patent is subject to a terminal disclaimer.

(21) Appl. No.: 14/643,749

(22) Filed: Mar. 10, 2015

(65) Prior Publication Data
US 2015/0182763 A1 Jul. 2, 2015

Related U.S. Application Data

(60) Division of application No. 12/116,845, filed on May 7, 2008, now Pat. No. 9,011,336, and a continuation-in-part of application No. 12/116,845, filed on May 7, 2008, now Pat. No. 9,011,336, which is a continuation-in-part of application No.
(Continued)

(51) Int. Cl.
| | |
|---|---|
| *A61N 7/02* | (2006.01) |
| *A61N 7/00* | (2006.01) |
| *A61B 18/14* | (2006.01) |
| *A61B 18/20* | (2006.01) |
| *A61B 17/22* | (2006.01) |
| *A61B 8/00* | (2006.01) |
| *A61B 34/30* | (2016.01) |

(52) U.S. Cl.
CPC ............... *A61N 7/022* (2013.01); *A61N 7/00* (2013.01); *A61B 8/4281* (2013.01); *A61B 18/14* (2013.01); *A61B 18/20* (2013.01); *A61B 34/30* (2016.02); *A61B 2017/22024* (2013.01); *A61B 2017/22028* (2013.01); *A61N 7/02* (2013.01); *A61N 2007/0008* (2013.01); *A61N 2007/0052* (2013.01); *A61N 2007/0078* (2013.01)

(58) Field of Classification Search
None
See application file for complete search history.

(56) References Cited

U.S. PATENT DOCUMENTS

| | | | | |
|---|---|---|---|---|
| 4,569,231 A | * | 2/1986 | Carnes | G01N 29/348 73/626 |
| 5,520,188 A | * | 5/1996 | Hennige | A61B 8/0833 310/367 |

(Continued)

OTHER PUBLICATIONS

Deane, "Safety id diagnostic ultrasound in fetal scanning" 2002, Doppler in Obstetrics.*

*Primary Examiner* — Yi-Shan Yang
(74) *Attorney, Agent, or Firm* — Quarles & Brady LLP

(57) ABSTRACT

A method and system for treating tissue with a combined therapy profile is disclosed. In one exemplary embodiment, ultrasound energy is used to treat numerous depths of tissue within a region of interest and the spatial and temporal properties of the ultrasound energy are varied for more effective treatment. The method and system of the present invention are configured to treat all of the tissue from the surface on down and not spare intervening tissue.

10 Claims, 14 Drawing Sheets

Related U.S. Application Data

10/944,500, filed on Sep. 16, 2004, now Pat. No. 7,824,348.

(60) Provisional application No. 60/916,475, filed on May 7, 2007.

(56) References Cited

U.S. PATENT DOCUMENTS

| | | | | |
|---|---|---|---|---|
| 5,558,092 | A * | 9/1996 | Unger | A61B 8/0833 600/439 |
| 6,042,556 | A * | 3/2000 | Beach | A61N 7/02 600/437 |
| 6,315,741 | B1 * | 11/2001 | Martin | A61B 8/4218 601/3 |
| 6,413,255 | B1 * | 7/2002 | Stern | A61B 18/14 606/41 |
| 2005/0137656 | A1 * | 6/2005 | Malak | A61N 5/0616 607/88 |
| 2005/0154314 | A1 * | 7/2005 | Quistgaard | A61B 8/00 600/459 |
| 2008/0228104 | A1 * | 9/2008 | Uber | A61B 10/0233 600/567 |
| 2008/0255478 | A1 * | 10/2008 | Burdette | A61N 7/02 601/2 |

* cited by examiner

METHOD AND SYSTEM FOR COMBINED ENERGY THERAPY PROFILE

CROSS-REFERENCE TO RELATED APPLICATION

This application is a divisional application claiming priority to U.S. patent application Ser. No. 12/116,845 filed May 7, 2008, which claims benefit of U.S. Provisional Patent Application 60/916,475 filed May 7, 2007 and this divisional application claims priority to U.S. patent application Ser. No. 12/116,845 filed May 7, 2008 which is a continuation-in-part of U.S. patent application Ser. No. 10/944,500 filed Sep. 16, 2004 and has patented as U.S. Pat. No. 7,824,348 on Nov. 2, 2010.

FIELD OF INVENTION

The present invention is directed to a method and system for treatment utilizing energy such as ultrasound energy. Specifically, the present invention is directed at treating tissues at various locations with ultrasound energy wherein the ultrasound energy is applied at different levels at different locations within the tissue.

BACKGROUND OF THE INVENTION

Energy, such as ultrasound energy, can be applied to treat tissue or perform traditionally invasive procedures in a non-invasive manner. The application of ultrasound energy provides both thermal and/or mechanical effects that help treat certain ailments such as acne and enable many traditional invasive procedures to be performed non-invasively.

Current ultrasound devices provide energy to tissue within a region of interest. The energy is emitted from an ultrasound system and travels a certain depth within the tissue and has an effect on the tissue. The effect can be ablative, coagulative, non-ablative, or non-coagulative and is generally caused by the thermal and/or mechanical properties that ultrasound has on tissue. Thermal properties increase the temperature of the tissue at the region of interest while the mechanical effects are achieved by cavitation, streaming, radiation force, and other natural mechanical effects of ultrasound.

Further, ultrasound energy has certain spatial and temporal properties when it is applied to the region of interest. The "temporal" properties refer to the time that the ultrasound energy is applied while the "spatial" properties refer to the space within the tissue that is affected by the ultrasound energy at a specific moment in time.

While effective, existing ultrasound devices only affect a specific portion of the tissue at a certain depth within the region of interest based upon the configuration of the ultrasound device. For example, an ultrasound device might be configured to affect an area five millimeters below the surface of the skin. The tissue from the surface of the skin to the depth of five millimeters is spared and not treated by the ultrasound energy. Sparing these intervening spaces of tissue hinders the overall beneficial effect of ultrasound as treatment of this intervening tissue increases ultrasound treatment's overall efficacy.

Therefore, it would be beneficial to provide an ultrasound device and treatment method that treats multiple areas of tissue in a region of interest including intervening tissue and even the distal layer of tissue. It would also be advantageous to provide a system and method that treated numerous depths of tissue by varying the spatial and temporal effects of ultrasound at different depths such has having ablative or coagulative ultrasound applied to certain depths of tissue while non-ablative ultrasound is applied to other depths of tissue.

SUMMARY OF INVENTION

A method and system for creating a combined energy profile by providing energy to tissue at different locations within a region of interest is provided. In an exemplary embodiment, the energy is ultrasound energy and it is provided at various locations and/or depths to conduct traditionally invasive procedures non-invasively by utilizing the thermal and/or mechanical effects of ultrasound energy. In certain exemplary embodiments, ultrasound energy with different spatial and temporal characteristics is applied to a region of interest ("ROI") to treat the ROI.

An exemplary system and method that provides ultrasound energy with different spatial characteristics creates different effects at different locations and/or depths within the tissue being treated. For example, ultrasound energy may be applied with a larger geometric shape at one depth and a smaller geometric shape at another depth without sparing the intervening tissue from the skin's surface to the deepest depth of ultrasound penetration. In certain exemplary embodiments, the application of ultrasound energy with differing spatial characteristics can increase the overall temperature at the ROI with less energy use.

Further, the time that the ultrasound energy is applied can also change the effects of the ultrasound energy at different tissue locations or depths. In one exemplary embodiment, energy can be applied at longer times at certain depths and shorter times at other depths without sparing intervening tissue. These temporal changes in the application of ultrasound energy can affect the results of the ultrasound treatment at the ROI.

In certain exemplary embodiments, both the temporal and spatial characteristics of ultrasound energy effect the overall treatment provided. In yet other embodiments, only the temporal changes effect the treatment. Still in yet other embodiments, only the spatial characteristics effect the treatment.

Various different ultrasound systems configured to provide the combined energy profile fall within the scope of the present invention. In one exemplary embodiment, an ultrasound system with a transducer probe comprising different transduction elements is provided. Each transduction element is capable of producing ultrasound energy for different time lengths and with a different geometric pattern.

Applying ultrasound energy at different spatial and temporal levels increases the temperature and/or utilizes the mechanical effects of ultrasound energy throughout the entire ROI from the surface of the skin to the deepest location of ultrasound energy penetration without sparing intervening tissue. Treating a ROI with a combined energy profile can be highly effective at treating certain ailments.

For example, acne at a ROI can affect multiple depths of tissue and acne can be treated at the top of the tissue where pimples form by applying ablative ultrasound energy to the top portion of the tissue. The various subcutaneous tissues below the surface of the skin can also be treated with non-ablative ultrasound energy to treat individual pilosebaceous glands that cause the acne.

BRIEF DESCRIPTION OF THE DRAWINGS

The subject matter of the invention is particularly pointed out in the concluding portion of the specification. The invention, however, both as to organization and method of operation, may be best understood by reference to the following description taken in conjunction with the accompanying drawing figures, in which like parts may be referred to by like numerals.

DETAILED DESCRIPTION

The present disclosure may be described herein in terms of various functional components and processing steps. It should be appreciated that such components and steps may be realized by any number of hardware components configured to perform the specified functions. For example, certain embodiments may employ various medical treatment devices, visual imaging and display devices, input terminals and the like, which may carry out a variety of functions and be capable of emitting ultrasound energy for imaging or treatment or combinations thereof.

Figure 1A:
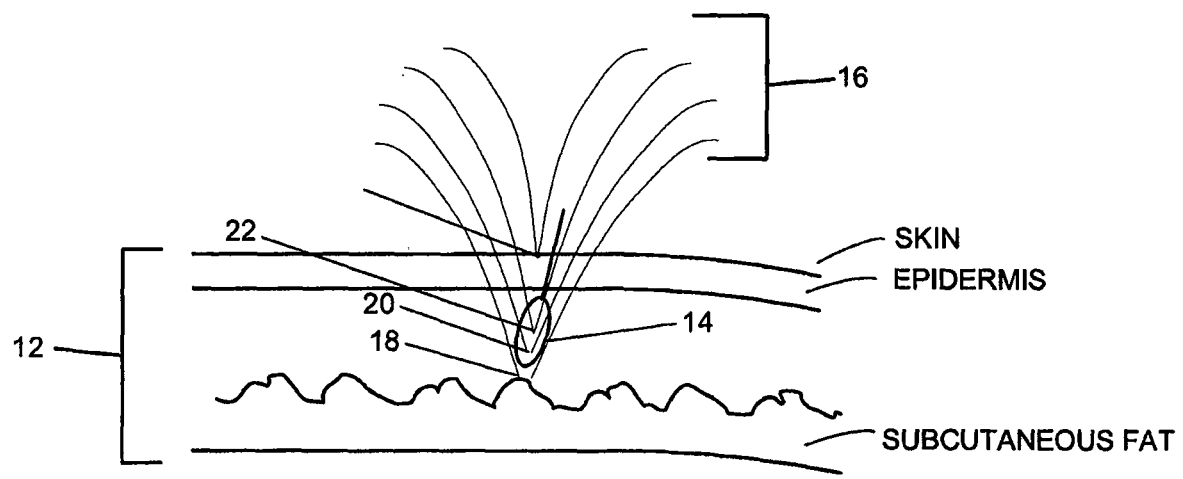
FIGS. 1A-1B illustrate a schematic diagram of tissue that can be treated in accordance with an exemplary embodiment of the present invention.
Figure 1B:
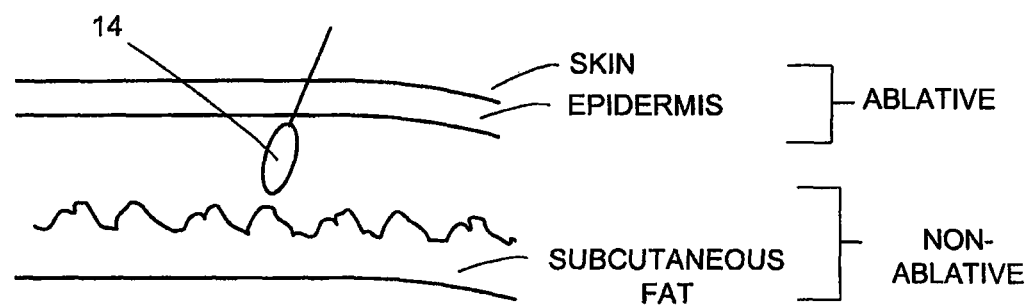
Figure 4:
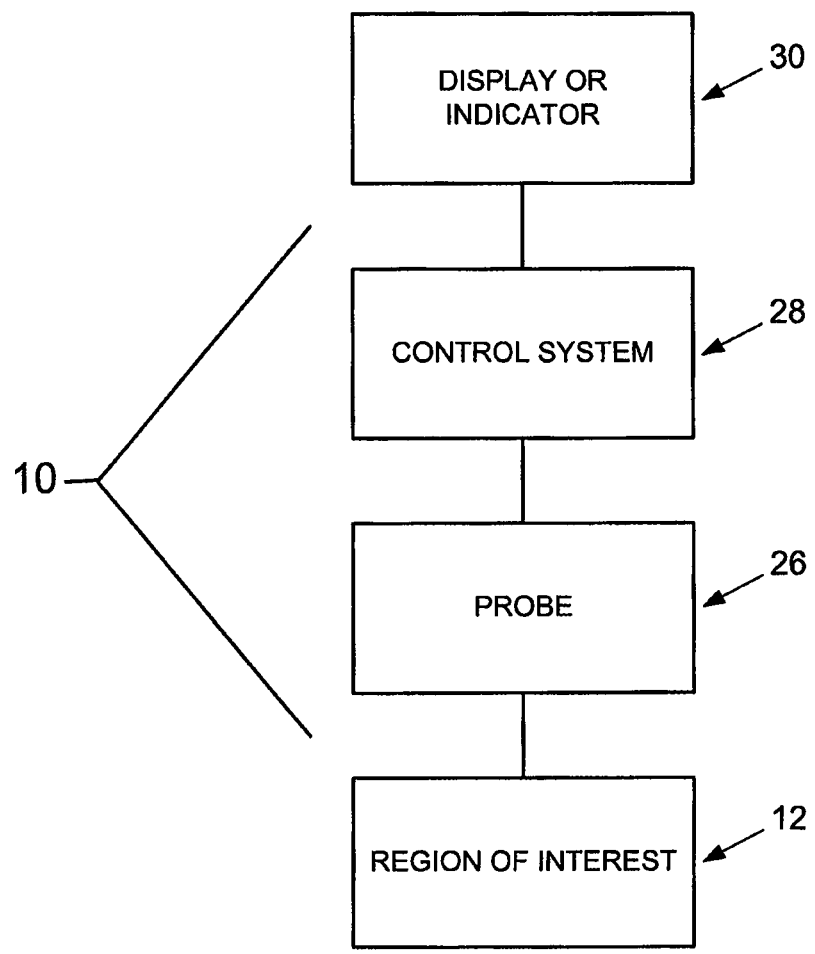
FIG. 4 illustrates a block diagram of a treatment system in accordance with an exemplary embodiment of the present invention.

With reference to FIGS. 1A, 1B, and 4, a method and system is disclosed for providing a combined therapy profile to several tissue depths in a ROI. In one exemplary embodiment, an energy emitting system such as an ultrasound system 10 can be used to provide therapeutic treatment to two or more tissue depths by emitting ultrasound energy with different spatial and temporal properties to different depths or areas within ROI 12. System 10 and the related method of the present invention apply ultrasound energy 16 to ROI 12 at the surface of the patient's skin and ultrasound energy 16 travels from the surface to a location within ROI 12 and treats all the tissue within ROI 12 with a combined energy profile without sparing any of such tissue.

With particular reference to FIGS. 1A and 1B, ROI 12 can comprise an inner treatment region, a superficial region, a subcutaneous region of Interest and/or any other region of interest in between an inner treatment region, a superficial region, and/or a subcutaneous region within a patient. In various exemplary embodiments, ROI 12 comprises at least one pilosebaceous unit 14 and an associated sebaceous gland. Throughout this application, reference to a "pilosebaceous unit" includes all the contents of the pilosebaceous unit 14 and related sebaceous gland.

Further, ROI 12 can include multiple layers or types of tissue such as, but certainly not limited to, skin, fat, muscles, tendons, cartilage, ligaments, the superficial muscular aponeurotic system, other fibrous or connective tissues, the dermis, epidermis, organ tissues, mucous membrane, hair bulb, hair shaft, hair follicle between the hair bulb, apocrine sweat glands, eccrine glands lying within the dermis, fat or muscle, tumors, and/or any other tissue of Interest.

Further, ROI 12 can be limited to specific depths such as 0-20 millimeters or it can deeper into the body. In one exemplary embodiment, ROI 12 is at a depth in the range of 0.2 to 8 millimeters while in another exemplary embodiment, ROI 12 is at a depth of 0.3 to 6 millimeters.

Alternatively, ROI 12 can be limited to the surface of the skin or immediately below the surface, or areas between the surface and greater depths within the body. While only one ROI 12 is depicted, a plurality of ROIs 12 can be treated by the system in an exemplary embodiment. Also, other glands can be treated by the method and system of the present invention. These glands comprise sweat glands, endocrine glands, and other glands. Therefore, the method and system of the present invention can be used to treat acne, oily skin and hair, as well as other ailments. ROI 12 may also consist of one more organs, such as skin, or a combination of tissues either superficial or deep within the body.

In an exemplary embodiment, energy such as ultrasound energy 16 is emitted from system 10 at multiple depths throughout ROI 12 to target numerous depths of tissue within a specific ROI 12. In addition to ultrasound energy 16, other energy forms such as photon-based energy such as laser energy, radio frequency energy (certain examples of radio frequency include monopolar and bipolar radio-frequency current), mechanical energy such as massage or other vibration-based energy and other energies can be used and fall within the scope of the present invention. Further, various light energy can be used in connection with ultrasound energy 16 to treat ROI 12. Certain exemplary frequencies of light are in the range of 400 nm to various wavelengths for infra-red light can be used.

For example, blue light at a wavelength of approximately 400 to 450 nm can be used to pre-treat ROI 12 before the application of ultrasound energy 16 or blue light of this wavelength can be used with ultrasound to increase the efficacy of treatment. In another embodiment, visible light in the range of 600 to 1350 nm can be used with the ultrasound during treatment.

Multiple depths of tissue within ROI 12 are treated from the surface down to the deepest point of ultrasound energy penetration and no intervening tissue is spared in one embodiment of the present invention. For example, ultrasound energy 16 from one source may have a spatial characteristic of affecting an area 15 millimeters in diameter 5 millimeters below the surface of the skin while ultrasound energy from another source may affect an area 9 millimeters below the surface of the skin with an area of 30 millimeters in diameter.

Various different time frames for ultrasound energy 16 emissions can be used in the present invention. Certain exemplary time frames include ranges of approximately fifty microseconds to fifteen minutes. Another exemplary time range is five hundred milliseconds to sixty seconds and yet another exemplary time frame is one second to sixty seconds. Numerous other time frame ranges can be implemented depending on the particular treatment application desired.

Moreover, the temporal characteristics of ultrasound energy 16 affecting ROI 12 can be changed for each location within the total area that comprises ROI 12. For example, ultrasound energy 16 that is directed 5 millimeters below the surface of the skin may only be emitted for 10 seconds while ultrasound energy 16 that is directed 9 millimeters below the surface of the skin may be emitted for 20 seconds. In other exemplary embodiments, these temporal properties of ultrasound energy 16 can be changed so that ultrasound energy 16 is pulsed for a certain duration. The time duration of each pulse of ultrasound energy can be changed as well. For example, ultrasound energy 16 can be emitted in 20 one second pulses at a depth of 5 millimeters below the surface of the skin and at 10 four second pulses at a depth of 10 millimeters below the surface of the skin. The different spatial and temporal properties of ultrasound energy 16 can be changed for each location and/or depth within a total ROI 12 to create a combined temperature profile.

As depicted in FIG. 1A and according to an exemplary embodiment of the present invention, ultrasound energy 16 is emitted and reaches different levels of tissue. As shown, some ultrasound energy 16 reaches a depth within subcutaneous fat at location 18. At locations 20 and 22, ultrasound energy reaches 16 a level to place it directly in the area of pilosebaceous unit 14 and its contents. As show in FIG. 1B, ablative energy may be applied near the surface while non-ablative energy is applied at non-ablative levels at deeper depths.

There are numerous possible medical applications for the system and method of the present invention. Many treatments effectuated by the method and system of the present invention result from increased blood perfusion at ROI 12 and the associated benefits of increased perfusion. For example, the application of ultrasound energy 16 at a specific location within ROI 12 can result in localized perfusion.

The increased perfusion can assist and/or stimulate numerous effects such as epidermal stimulation and a processes known as "colleganesis" or increasing the amount of collagen at ROI 12. Increasing perfusion also brings more of the body's natural repair cells (as discussed herein) to ROI 12 and that can assist with cell regeneration as well as other cellular repair processes and fibroblast activity. Increasing perfusion at ROI 12 also increases epidermal thickness and dermal mass. Other benefits from increasing blood perfusion are better skin tone and texture.

The application of ultrasound energy 16 also decreases certain conditions or ailments. For example, applying ultrasound energy 16 decreases pore size and blemishes (whether the blemishes are associated with acne or not). Other ailments or conditions that can be decreased by the application of ultrasound energy include, but are certainly not limited to, vascular defects, superficial wrinkles, uneven complexion, dischromia/blotchiness, and certain gland activity (such as the sebaceous gland).

The application of ultrasound energy 16 at higher levels powerful enough to cause ablation or coagulation at the skin surface or at greater depths within ROI 12 produces other effects. These effects can comprise the removal of warts, scars, moles, corns, calvi or calluses from ROI 12. Shaving bumps or "pseudofolliculitis barbae" can be treated or prevented with the method and system of the present invention. In this regard, the bumps can be ablated from the human body by applying ultrasound energy 16 at ablative levels or the bumps can be treated or prevented by applying ultrasound energy 16 at deeper depths at non-ablative levels to increase perfusion to the area with shaving bumps to treat the cause of the shaving bumps such as infected glands.

Moreover, the application of ultrasound energy 16 at ROI 12 can create lesion by heating or burning tissue, and/or cavitation within ROI 12.

In the examples set forth above, while certain tissues are being removed from ROI 12 by applying ultrasound energy 16 at ablative levels, ultrasound energy 16 at lower, non-ablative levels can be applied deeper within ROI 12. For example, ultrasound energy 16 can be applied at ablative or coagulative levels to remove a mole from the surface of the skin while lower, non-ablative and non-coagulative ultrasound energy can be applied at deeper depths to increase blood perfusion at those depths. Changing the temporal and spatial parameters of the application of ultrasound energy 16 at different locations determines whether or not it is applied at an ablative or non-ablative level.

Various other effects resulting from the application of ultrasound energy 16 at ROI 12 comprise peaking out inflammation or edema at ROI 12. Further, increased angiogenesis (the growth of blood vessels) can result by the application can result from applying ultrasound energy 16 to ROI 12.

As described herein, applying ultrasound energy 16 at ROI 12 can have curative and non-curative effects. Further, while numerous examples of treatments have been described herein, other treatments can be effectuated and fall within the scope of the present invention. Further, in one exemplary embodiment, two or more types of treatment can occur simultaneously at ROI 12. For example, a mole can be burned off at the skin's surface while increased angiogenesis occurs at a deeper level within the tissue at ROI 12.

In an exemplary embodiment, the spatial and temporal properties of ultrasound energy 16 can be changed to effectively treat acne and the associated pilosebaceous unit 14. Specifically, ultrasound energy 16 can be applied with spatial and temporal properties that result in ablation of tissue at the surface of the skin by raising the temperature at the skin's surface above 60° C. for approximately one second, which causes ablation, or above any time-temperature threshold. According to one exemplary embodiment, ultrasound energy 16 is applied at non-ablative levels below the surface in ROI 12 near pilosebaceous unit 14. Ultrasound energy is applied at non-ablative levels by varying the spatial and temporal characteristics of ultrasound energy 16 to levels where they do not raise the temperature above ablative levels or 60° C.

Further, with reference to FIG. 1B, applying ultrasound energy 16 at various depths within ROI 12 can create a zone within the tissue where ablation or coagulation may occur. Another region (either above or below), can receive ultrasound energy at non-ablative levels with the same ROI 12. Treating areas or zones within ROI 12 with different levels of ultrasound energy provides a combined treatment effect as explained herein.

In another exemplary embodiment, ultrasound energy 16 is applied at different depths or locations within ROI 12 non-simultaneously. In this exemplary embodiment of non-simultaneous ultrasound energy 16 emissions, ultrasound energy 16 from one source can be applied to raise the temperature at certain predetermined depth to a certain level. Ultrasound energy from another source aimed to target an area within ROI 12 above the first area targeted by the first source. Because the first area in ROI 12 is already heated and adjacent to the second area, the second area is in effect pre-heated and less ultrasound energy 16 is required to heat the second area. By utilizing ultrasound energy 16 from two sources and applying it in this stepped form, less overall energy is needed than if energy was used from a single source.

Figure 2:
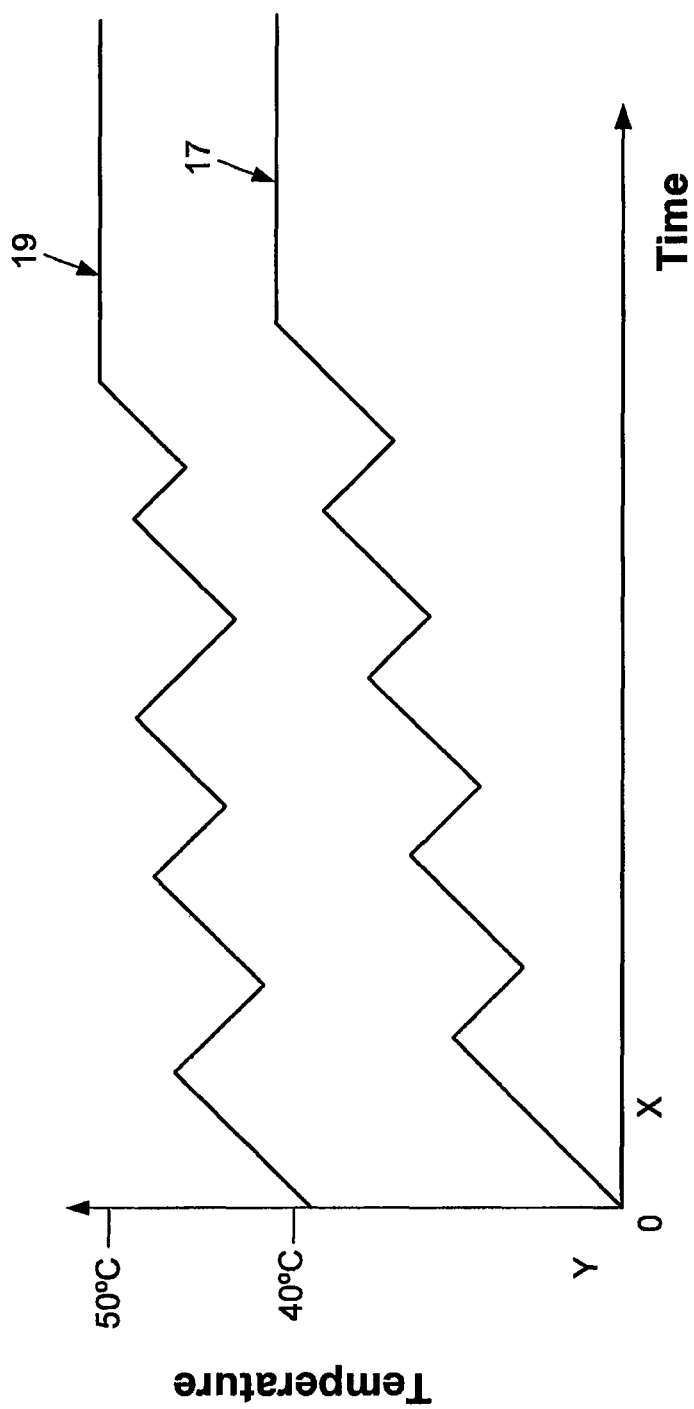
FIG. 2 illustrates a graph showing the temperature increase over a given time period in accordance with an exemplary embodiment of the present invention.

FIG. 2 illustrates a graph of this type of temperature increase. As shown on the graph, the temperature is represented on the "y" axis while the time is represented on the "x" axis. Line 17 represents the temperature increase caused by a first emission of ultrasound and line 19 represents the temperature increase caused by a second emission of ultrasound. As shown in this exemplary embodiment, the temperature is raised to a new base or threshold level of 40° C. by application of the first emission of ultrasound energy 16. This increased threshold enables the second emission of ultrasound to raise the temperature to a still higher level of 50° C. as shown by line 19.

Figure 3A:
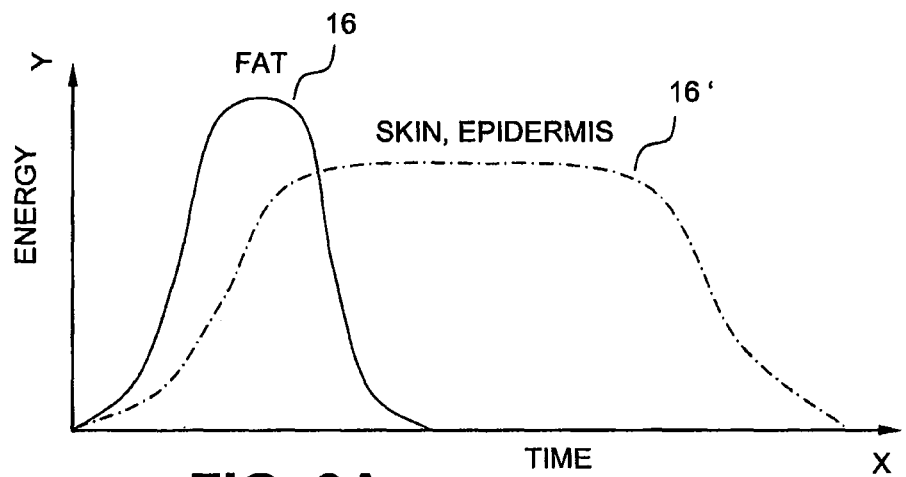
FIGS. 3A-3C illustrate graphs that show the spatial and temporal changes of ultrasound energy at various tissue depths in accordance with one exemplary embodiment of the present invention.
Figure 3B:
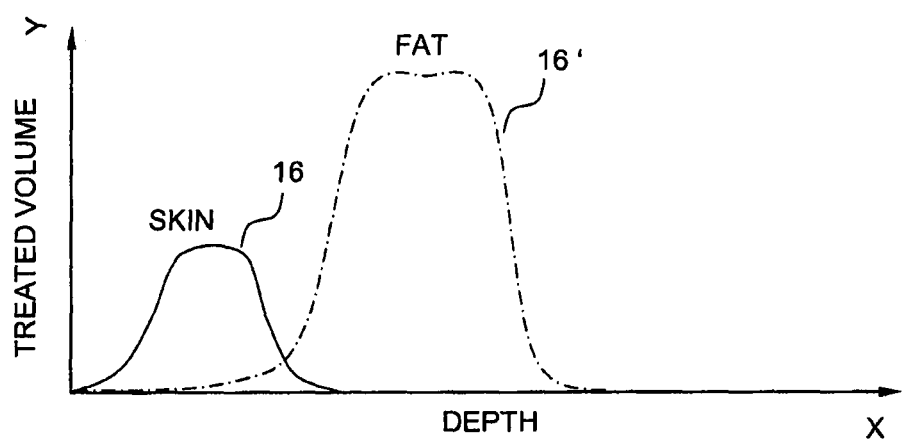
Figure 3C:
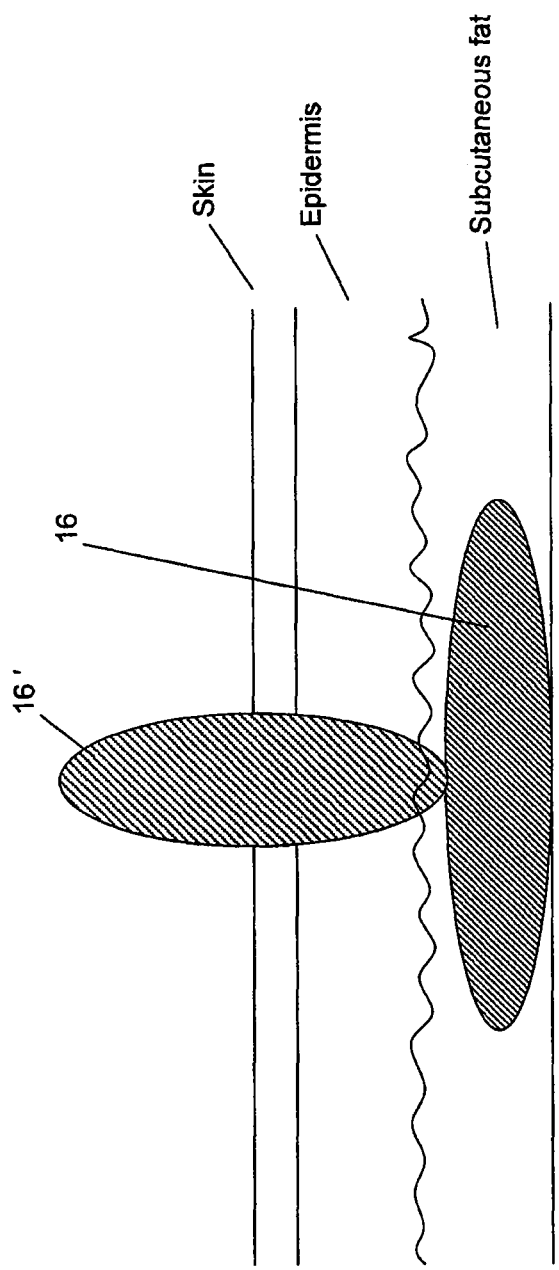

FIGS. 3A-3C illustrate various different examples of the spatial and temporal applications of energy such as ultrasound energy 16 in different exemplary embodiments of the present invention. With particular reference to FIG. 3A, temporal changes for ultrasound energy 16 applied to fat and ultrasound energy 16' applied to the skin and epidermis can vary. The "Y" axis represents the amount of energy applied within ROI 12 and the "X" axis represents the time period that ultrasound energy 16 is applied.

In this example, ultrasound energy 16' is applied for a longer time period near the skin and epidermis while ultrasound energy 16 is applied for a short time period in the subcutaneous fat of ROI 12. The temporal characteristics of ultrasound energy 16 can be changed in other exemplary embodiments of the present invention depending on the treatment desired.

With reference now to FIG. 3B, the spatial properties of ultrasound energy within ROI 12 at a given moment in time are shown. The "Y" axis represents the treated volume of tissue while the "X" axis represents the depth of ultrasound energy 16. As shown in this exemplary embodiment, ultrasound energy 16 applied near the skin can treat a volume less than the volume treated by ultrasound energy 16' applied to the subcutaneous fat. The spatial properties illustrated in this graph can also be varied depending on the treatment desired in other exemplary embodiments of the present invention.

FIG. 3C also depicts a spatial distribution of ultrasound within (and proximal to) ROI 12 at a given period of time. As shown, there are two different patterns of ultrasound energy 16 and 16'. The pattern of ultrasound energy shown as 16 is deep and wide within ROI 12 while the pattern shown by 16' is long and narrow and affects the upper portion of tissue in ROI 12. The different patterns of ultrasound energy can be applied by utilizing two different transduction elements 50 as explained herein. In one exemplary embodiment, the patterns are applied simultaneously within ROI 12 and in another exemplary embodiment the patterns are applied at different times. When the patterns are applied at different times, the pattern of ultrasound energy 16 can be used to increase the base temperature of ROI and increase the effect of the pattern of ultrasound energy 16' as explained above.

The application of different levels of ultrasound energy 16 at different depths of tissue creates a combined therapy profile at ROI 12. For instance, instead of merely treating acne by targeting pilosebaceous unit 14 and surrounding area with energy at ablative or non-ablative levels (as described in co-pending U.S. patent application Ser. Nos. 11/163,177 and 11/738,682 entitled Method For Treating Acne and Sebaceous Glands and Method and System for Non-Ablative Acne Treatment and Prevention respectively wherein both such applications are herein incorporated by reference in their entirety) to destroy or otherwise effect pilosebaceous unit 14 and its contents, all of the tissue at ROI 12 can be targeted to treat and prevent acne or other ailments.

For example, pilosebaceous unit 14 can be treated with ablative levels to destroy it and prevent unwanted sebum production. With the pilosebaceous gland destroyed or otherwise inhibited, sebum production is halted and future acne is prevented from developing. But, scarring, scars, blackheads, whiteheads, cysts, and scarring may still be present at the top layers of the skin such as the dermis. These layers of tissue can be treated by the application of ultrasound energy 16 at lower, non-ablative, and non-coagulative levels than what is applied at the depth of pilosebaceous unit 12.

Applying ultrasound energy 16 at lower levels at the surface of the skin heats the surface. The body's natural reaction to this increased temperature at ROI 12 is to increase blood perfusion to the ROI 12. The increased blood perfusion delivers more blood to ROI 12. The increased blood at ROI 12 results in increased number of repair cells contained within the blood to be delivered to ROI 12. Specifically, the more blood that flows to ROI 12, the more fibroblast cells and other therapeutic leucocyte cells (white blood cells) such as lymphocytes, macrophages, and neutrophils are at ROI 12 to treat current acne and prevent future acne from developing. The repair cells treat existing acne by helping acne lesions heal faster. Future acne is prevented because more nutrients at ROI 12 are able to fight acne-causing bacteria such as P-acnes.

Therefore, in this example, acne is treated by targeting multiple tissue depths at ROI 12. The depth within ROI where pilosebaceous unit 14 is located is treated with ultrasound energy 16 at one level to cease sebum production to prevent future acne from developing. Moreover, the layer where the effects of acne are seen (at the skin) is also treated with ultrasound energy 16 to help heal the scars and visible effects of acne.

In another exemplary embodiment, the temperature range within the depths of tissue can be reversed. In this exemplary embodiment, energy such as ultrasound energy 16 is applied at ablative or coagulative levels at the surface of the skin and at lower, non-ablative and non-coagulative levels at deeper depths. In this exemplary embodiment, a mole or cyst can be "burned" off of the skin at the ROI while the application of energy at deeper depths can cause increased blood perfusion which heals the area once the mole or cyst is removed and/or treated.

Applying energy such as ultrasound energy 16 at multiple depths and at different levels simultaneously treats all the tissue at the ROI 12 with the thermal and/or mechanical effects of ultrasound. The thermal effects raise the temperature above the body's normal temperature. These temperature ranges can be in whatever range needed to affect a particular result. According to the present invention, a certain amount of ultrasound energy 16 can be applied at a pre-determined depth to raise the temperature at that depth to achieve a certain result. Certain zones with a given temperature can be created at various levels of tissue depending on the level of energy provided.

For example, it might be necessary to raise the temperature to fifty degrees or more at the surface and dermal layer of tissue to burn off a mole, tumor, or other piece of unwanted skin or tissue. During this application of ultrasound energy 16, it may also be desirable to raise the temperature at a deeper depth much lower, to only five or ten degrees above the body's normal temperature to achieve a result such as increased blood perfusion. The lower temperature at one zone or layer within the tissue and higher temperature at another zone treats the entire ROI 12.

Besides temporal changes at various depths within the tissue, ultrasound energy 16 also has certain mechanical effects that can be used for treatment. In an exemplary embodiment, these mechanical effects comprise cavitation, streaming, radiation force, oscillatory forces, and sheer stress on cellular membranes of cells that comprise tissue that is being targeted. These mechanical effects such as cavitation and streaming create various forces that contact cellular walls. For example, when using the method and system of the present invention to treat acne, ultrasound energy can be used to contact the cellular walls of P-acnes and other acne causing organisms which damage or kill them. Further, these mechanical effects can also help drive medicinal creams and other agents into tissue cells to better effectuate treatment and assist in transdermal drug delivery for acne or other forms of treatment.

Just as the case with thermal effects, these mechanical effects may be provided at certain depths and zones within ROI 12. Applying energy at a certain level at a certain depth is used to cause certain mechanical effects at that level. In an exemplary embodiment, the more ultrasound energy 16 applied, the more mechanical effects are realized. Lower energy results in fewer effects. For example, applying energy at greater levels at certain locations within the tissues will result in greater mechanical effects such as streaming and cavitation which may be needed at those locations to achieve a certain result.

The amount of energy can vary at different levels and cause specific effects at one level while causing another effect at another level simultaneously. This treatment at different levels can create a combined treatment that works with or independently of the thermal effects described above. For example, providing ultrasound energy 16 at higher levels may be needed to cause sufficient cavitation and/or streaming at the depth of tissue where a pilosebaceous unit 14 is located and may be necessary to destroy bacteria within the pilosebaceous unit to prevent and cure acne.

As ultrasound energy 16 is being applied at sufficient levels to cause cavitation and/or streaming sufficient to destroy bacteria, lower energy levels could be applied at other area within ROI 12. Applying ultrasound energy 16 at lower levels at other depths and locations within ROI 12 may be needed to achieve other effects such as transdermal drug delivery. Transdermal drug delivery is achieved by using the mechanical effects to push medicines and other medicants into the tissue cells at ROI 12. Further, in an exemplary embodiment, the medicines can be contained within a coupling gel, cream, or other substance that is used to couple probe 26 or transducer to the patient's body at ROI 12.

An exemplary system 10 for a combined therapy profile treatment is provided and depicted in FIG. 4. In this exemplary embodiment, an ultrasound system comprising a probe 26, a control system 28, and a display system 30 is used to delivery energy such as ultrasound energy 16 to and monitor ROI 12. Other exemplary systems are disclosed in co-pending U.S. patent application Ser. No. 11/163,177 entitled "Method and System For Treating Acne and Sebaceous Glands" and U.S. patent application Ser. No. 10/950,112 entitled "Method and System For Combined Ultrasound Treatment," both of which are hereby incorporated by reference.

An exemplary probe 26 is a transducer that emits ultrasound energy into ROI 12 to heat ROI 12 at specific depths and/or cause certain mechanical effects at specific depths. A coupling agent is used to couple probe 26 to a patient's body in one exemplary embodiment. In another exemplary embodiment, suction is used to attach probe 26 to the patient's body.

Figure 5:
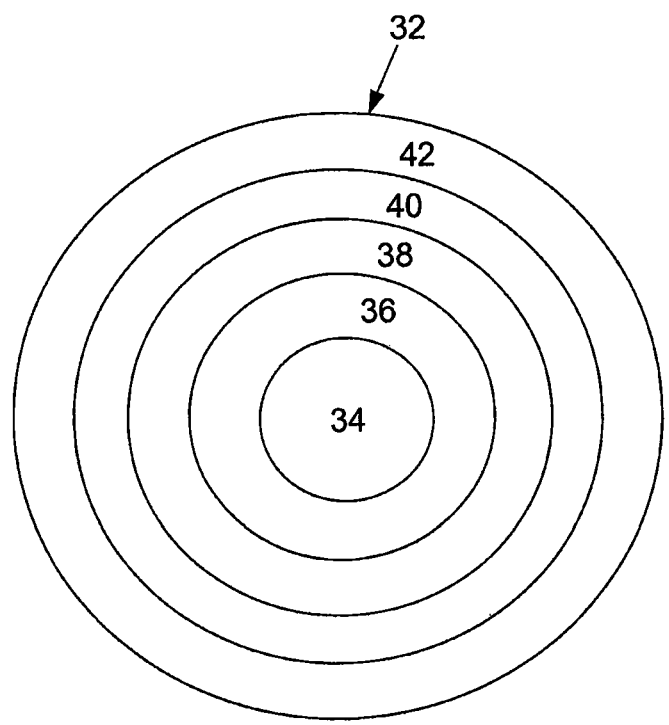
FIG. 5 illustrates an annular transducer array in accordance with an exemplary embodiment of the present invention.

With additional reference to FIG. 5, an exemplary probe 26 is an annular array 32 with numerous transduction elements disposed within rings 34, 36, 38, 40, and 42. In this exemplary embodiment, each transduction element is configured to emit ultrasound energy 16 at different spatial and/or temporal levels which is capable of achieving different effects within ROI 12. In this exemplary embodiment, the transducer is divided into numerous rings 34-42 and each ring contains a separate transduction element. For example, the transduction element in ring 36 may be capable of producing ultrasound energy 16 that reaches 5 mm below the skin's surface while the transduction element in ring 38 may be capable of reaching 10 mm below the surface of the skin. In another exemplary embodiment, each ring may have multiple transduction elements that may or may not emit energy at the same level within a ring.

The elements within the rings may be capable of emitting energy reaching 15 mm, 20 mm, and 25 mm below the skin's surface respectively in this exemplary embodiment. In order to reach a certain depth within ROI 12, each transduction element 50 is constructed so that it may emit ultrasound energy 16 to reach this depth. System 10 can emit ultrasound energy at various frequency ranges. Certain exemplary ranges include about 0.10 MHz to 100 MHz or more. More specifically, exemplary frequencies include about 0.15 MHZ and 0.2 MHz as lower frequencies and about 0.15 MHz to 100 MHz or more as higher frequencies. For example, in order to reach a depth of 0-15 mm, transduction element 50 has an operating power of about 10-100 watts and emits ultrasound energy 16 at a frequency of about 1-12 MHz. In order to reach a depth of about 0-20 mm, transduction element 50 has an operating power of about 20-200 watts and emits ultrasound energy at a frequency of about 1-9 MHz. Finally, to achieve a depth of about 0-25 mm, transduction element 50 has an operating power of about 1-120 watts and emits ultrasound energy 16 at a frequency of about 1-20 MHz.

Figure 6:
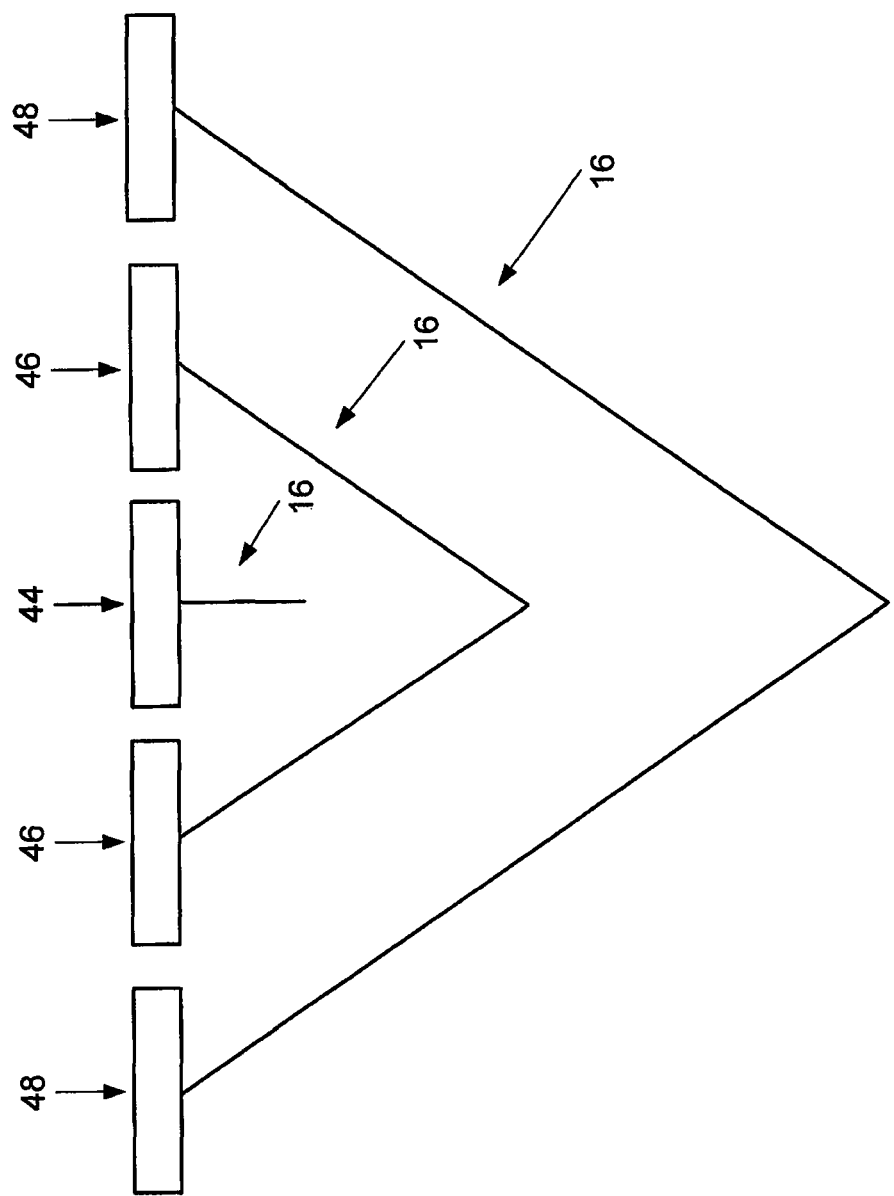
FIG. 6 illustrates an annular transducer array in accordance with an exemplary embodiment of the present invention.

With reference to FIG. 6 another exemplary annular array is show. In this exemplary embodiment, the annular array has three rings 44, 46, and 48 as shown. Each ring comprises a different transduction element 50 that is configured to emit ultrasound energy 16 with different temporal and/or spatial parameters. For example, ring 44 may be configured to emit ultrasound energy for a time period of 5 milliseconds, ring 46 may be configured emit ultrasound energy for 10 milliseconds, while ring 48 is configured to emit ultrasound energy for 15 milliseconds. In one exemplary embodiment, the time that ultrasound energy is emitted from each ring is controlled by control system 28. Emission of ultrasound energy 16 may be repeated at various times and depths to produce desired thermal and/or mechanical effects within ROI 12.

Energy such as ultrasound energy 16 can be emitted at various levels from each transduction element. These levels can be changed by varying the amount of energy emitted or the time it is emitted from system 10. For example, ultrasound energy 16 can be emitted at ablative or coagulative levels by being emitted at a high power for a short time or low power for a longer duration. The energy emission and time frames can be varied to achieve the desired level of energy emission. Moreover, the penetration depth of ultrasound energy 16 may be changed depending on which ring 46-48 it is emitted from. For example, as shown in FIG. 6, the ultrasound energy from ring 46 may only reach a shallow level compared to ultrasound energy from ring 48. Ultrasound energy 16 from ring 48 may be used to pre-heat ROI 12 before ultrasound energy 16 from ring 46 is emitted and thus create a profile as shown in FIG. 2.

In one exemplary embodiment, transduction elements 50 are configured to emit ultrasound energy at a focal depth of 3-4 millimeters. In other exemplary embodiments, a single transducer or probe with multiple elements 50 is configured to produce variable amounts of ultrasound energy. Specifically, a transducer can contain numerous elements 50 and each element 50 is constructed to emit ultrasound energy at different parameters. Certain exemplary parameters comprise the depth of ultrasound energy 16 penetrations, the power supplied to each element 50, the frequency of operation of each element 50, the focal strength or "F Number," the depth or focal depth, and energy. In one exemplary embodiment, transduction elements 50 are arranged in probe 26 in a specific manner to create a controlled, predictable emission of ultrasound energy 16. For example, a transducer can be constructed by providing elements to generate a known, predetermined pattern of ultrasound energy within ROI 12.

In another exemplary embodiment, transduction elements 50 are arranged within probe 26 to create a "cloud" of lesions within ROI 12 wherein each lesion has a different size and depth. According to this exemplary embodiment, different elements 50 are selected for their emission times, frequencies, focal depth, focal strength (F-number), energies and other relevant parameters discussed herein. The elements 50 are placed on a device that moves and enables the lesions to be placed at different locations within ROI 12 depending on the location of the elements relative to ROI 12.

In another exemplary embodiment, varying these parameters from one element 50 to another element 50 contained within probe 26 may create a pseudo random emission pattern of ultrasound energy 16. The creation of a pseudo random emission of ultrasound energy 16 creates a wide spatial and/or temporal band of therapeutic efficacy.

A time-temperature profile for the method can be modeled and optimized with the aid of the thermal dose concept. The thermal dose, or $t_{43}$, is the exposure time at 43° C. which causes an equivalent biological effect due to an arbitrary time-temperature heating profile. Typically an ablative lesion forms on the order of one second at 56° C., which corresponds to a thermal dose of one hundred and twenty minutes at 43° C. The same thermal dose corresponds to 50° C. for approximately one minute. Thus a non-ablative profile can contain high temperatures for very short times and/or lower temperatures for longer times or a combination of various time-temperature profiles. For example, temperatures as high as 56° C. for under one second or 46° C. for under fifteen minutes can be utilized. Such processes can be implemented in various exemplary embodiments, whereby one or more profiles may be combined into a single treatment.

In an exemplary embodiment the temperature is raised to a high level, such as approximately 50° C. or more and held for several seconds. In another exemplary embodiment, the temperature is raised to a high level, (for example greater than 50° C.), for under one second up to five seconds or more, and then turned off for under one second up to five seconds or more, and repeated to create a pulsed profile.

In another exemplary embodiment, the temperature is raised quickly to a high level (greater than 50° C.), and then dropped to a lower temperature (less than 50° C.), and then maintained at that temperature for a given time period such as one second up to several seconds or over a minute.

In another exemplary embodiment, the temperature is increased quickly to a high level ($T_{HIGH}$), whereby $T_{HIGH}$ is greater than 40° C., and the power to the system is turned off, but turned on again once the temperature drops below a lower threshold, ($T_{LOW}$), whereby $T_{LOW}$ is less than $T_{HIGH}$. Once the temperature reaches $T_{HIGH}$ again power to the system is turned back off and this process is repeated, in effect acting like a thermostat.

In another exemplary embodiment, the temperature is raised quickly to a high level ($T_{START}$), whereby $T_{START}$ is greater than 40° C. and then turned off, but turned on again before the temperature drops appreciably (i.e. by a few degrees) below $T_{START}$, whereby the temperature may then increase a small amount (i.e. by a few degrees) over $T_{START}$ before the power is turned off again. In such an exemplary embodiment the temperature quickly reaches a starting point and then may be allowed to increase to a higher temperature yet still remain in a non-ablative or coagulative regime before the treatment is ended.

Besides annular array 32 depicted in FIG. 5, other transducers and probes 26 could be used and fall within the scope of the present invention. Other exemplary arrays include truncated annular array, a linear array, a linear phased array, or a two dimensional phased array. Certain exemplary transducers comprise transducers that are configured to move in any vertical or horizontal direction or transducer with an adjustable angular altitude. Any transducer arrangement configured to emit ultrasound energy 16 to depths within the tissue now known or developed in the future can be used and fall within the scope of the present invention.

The ultrasound energy 16 emitted can be emitted in various energy fields. The energy fields can be focused, defocused, and/or made substantially planar by the transducer to provide a plurality of different effects. Energy can be applied at one or more points in one or more C-planes or C-scans by automated or manual movement. For example, a substantially planar energy field can provide a heating and/or pretreatment effect, a focused energy field can provide a more concentrated source of heat or hyperthermal effect, and a non-focused energy field can provide diffused heating effects. It should be noted that the term "non-focused" as used throughout is meant to encompass energy that is unfocused or defocused.

An exemplary transducer emits ultrasound energy for imaging or treatment or a combination of both imaging and treatment. In an exemplary embodiment, the transducer is configured to emit ultrasound energy at specific depths in within ROI 12 as described above.

With reference to FIGS. 7A-7D, a transducer can comprise one or more transduction elements 50 configured for facilitating treatment. Transduction elements 50 can comprise a piezoelectrically active material, such as lead zirconante titanate (PZT), or any other piezoelectrically active material, such as a piezoelectric ceramic, crystal, plastic, and/or composite materials, as well as lithium niobate, lead titanate, barium titanate, and/or lead metaniobate. In addition to, or instead of, a piezoelectrically active material, a transducer can comprise any other materials configured for generating radiation and/or acoustical energy. The transducer can also comprise one or more matching and/or backing layers configured along with a transduction element(s) 50 such as coupled to the piezoelectrically active material. The transducer can also be configured with single or multiple damping elements along with transduction element 50.

In accordance with an exemplary embodiment, the transduction element 50 of the transducer can be configured to be uniform thereby having a narrowband resonance frequency distribution. In accordance with another exemplary embodiment, transduction element 50 can also be configured with a variable thickness, and/or as a multiple damped device, thereby having a wideband resonance frequency distribution. For example, transduction element 50 of the transducer can be configured to provide a center operating frequency of a lower range, for example from approximately 1 kHz to 3 MHz. Transduction element 50 can also be configured to provide a center operating frequency of a higher range, for example from approximately 3 to 100 MHz or more. In yet other exemplary embodiments, transduction element 50 is configured to emit ultrasound energy 16 at a frequency in the range of 1-15 MHz. In yet other exemplary embodiments, transduction element 50 is configured to emit ultrasound energy 16 at a frequency in the approximate range of 0.5 to 100 MHz, and in still yet other exemplary embodiments, transduction element 50 is configured to emit ultrasound energy at a frequency in the approximate range of 0.75 to 25 MHz. Other exemplary frequencies are in the approximate range of 0.75 MHz to 1.75 MHz. Harmonics and sub-harmonics can also be used in various embodiments of the present invention.

The transducer can be configured as a single broadband transducer excited with at least two or more frequencies such as 4 MHz and 7 MHz to provide an adequate output for raising the temperature and or causing the mechanical effects within the ROI to the desired level. The transducer can also be configured as two or more individual transducers, wherein each of the transducers comprises a separate transduction element 50.

Moreover, in an exemplary embodiment, any variety of mechanical lenses or variable focus lenses, e.g. liquid-filled lenses, may also be used to focus and or defocus the energy field. For example, the transducer may also be configured with an electronic focusing array in combination with one or more transduction elements 50 to facilitate increased flexibility in treating the ROI. The array may be configured in a manner similar to the transducer. That is, the array can be configured as an array of electronic apertures that may be operated by a variety of phases via variable electronic time delays, for example, $T_1, T_2, T_3 \ldots T_j$. By the term "operated," the electronic apertures of the array may be manipulated, driven, used, and/or configured to produce and/or deliver energy in a manner corresponding to the phase variation caused by the electronic time delay. For example, these phase variations can be used to deliver defocused beams, planar beams, and/or focused beams, each of which may be used in combination to achieve different physiological effects in ROI 12.

Transduction elements 50 may be configured to be concave, convex, and/or planar. For example, in an exemplary embodiment depicted in FIG. 7A, transduction elements 50 are configured to be concave in order to provide focused energy for treatment of the ROI. Additional embodiments are disclosed in U.S. patent application Ser. No. 10/944,500, entitled "System and Method for Variable Depth Ultrasound Treatment", and again incorporated herein by reference.

In one exemplary embodiment, transduction elements 50 are therapy line-focused single elements. Further, arrays 56, 58, 60, and 62 noted below may further comprise at least one imaging element 50 or a combination of imaging elements with treatment elements 50. In another exemplary embodiment, multiple-element, multiple-delay transducers 50 can be multiple-element, multiple-delay transducers perpendicular to those shown in FIGS. 7A and 7B, whereby such perpendicular disposes transducers are therapy, imaging, or dual-mode imaging-therapy elements.

Figure 7A:
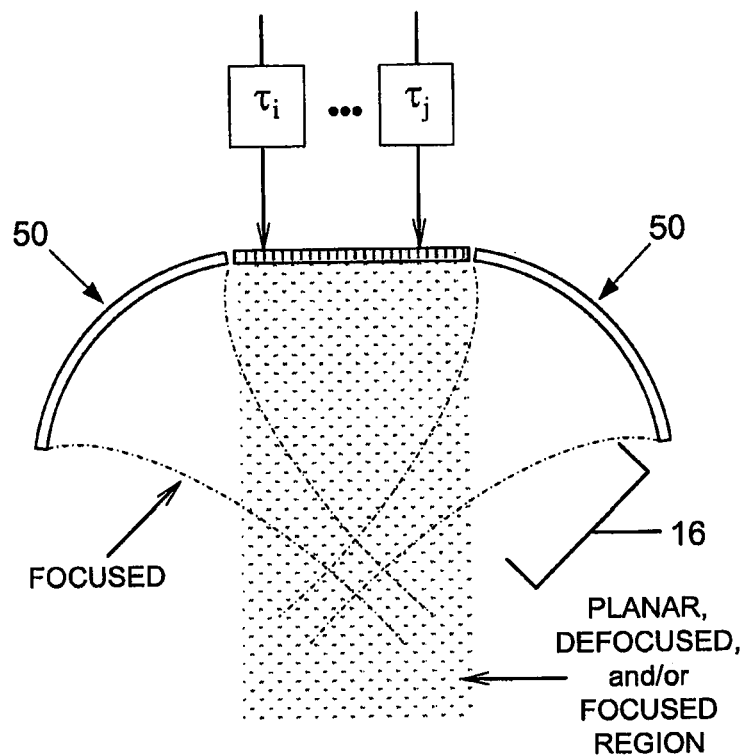
FIGS. 7A-7D illustrate cross-sectional diagrams of an exemplary transducer in accordance with various embodiments of the present invention.
Figure 7B:
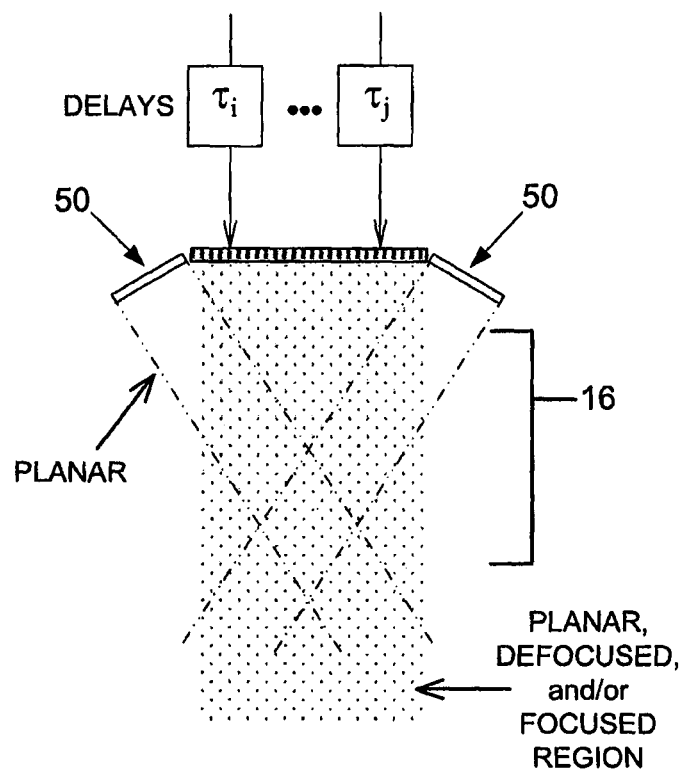

In another exemplary embodiment, depicted in FIG. 7B, transduction elements 50 can be configured to be substantially flat in order to provide substantially uniform energy to ROI 12. While FIGS. 7A and 7B depict exemplary embodiments transduction elements 50 configured as concave and substantially flat, respectively, transduction elements 50 can be configured to be concave, convex, and/or substantially flat. In addition, transduction elements 50 can be configured to be any combination of concave, convex, and/or substantially flat structures. For example, a first transduction element 50 can be configured to be concave, while a second transduction element 50 can be configured to be substantially flat.

Figure 7C:
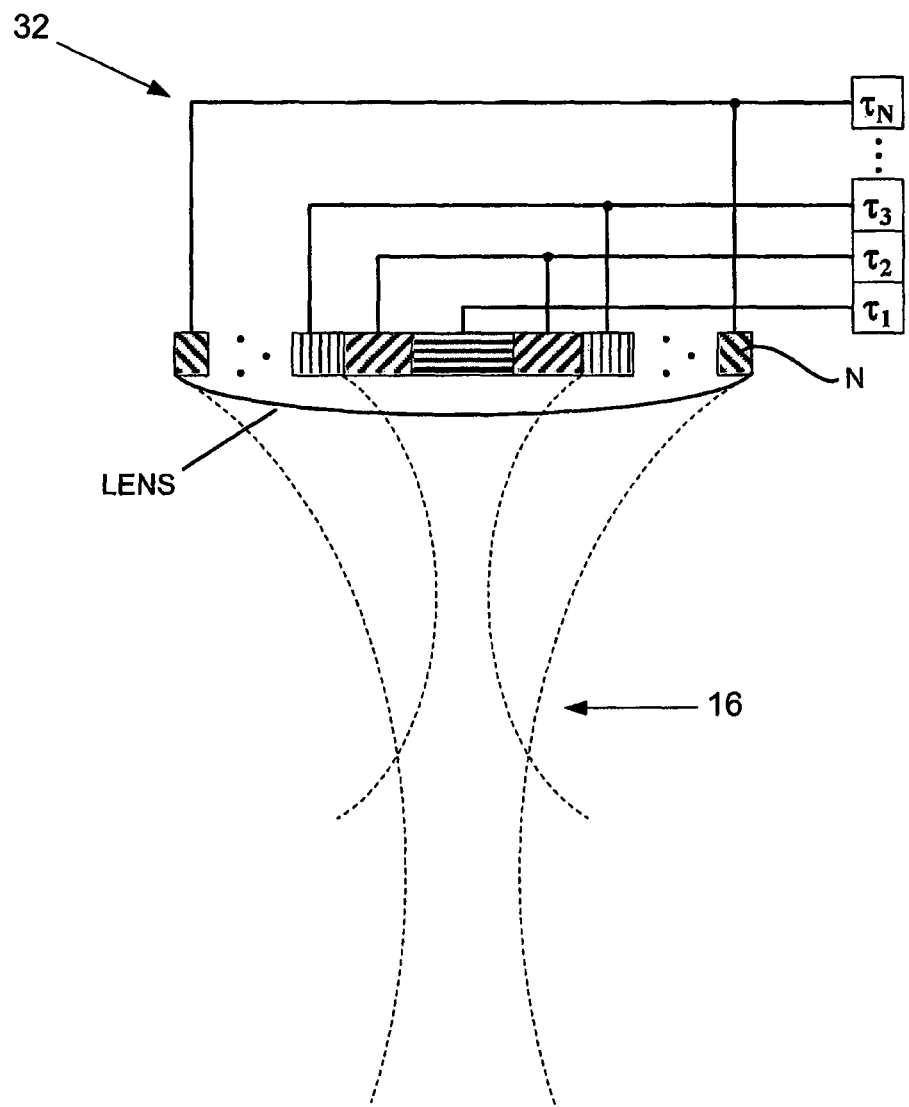

With reference to FIGS. 5, 6, and 7C, the transducer can also be configured as annular array 32 to provide planar, focused and/or defocused acoustical energy. The rings can be mechanically and electrically isolated into a set of individual elements, and can create planar, focused, or defocused waves. For example, such waves can be centered on-axis, such as by methods of adjusting corresponding transmit and/or receive delays, $T_1, T_2, T_3 \ldots T_N$. An electronic focus can be suitably moved along various depth positions, and can enable variable strength or beam tightness, while an electronic defocus can have varying amounts of defocusing. In accordance with an exemplary embodiment, a lens and/or convex or a concave shaped annular array can also be provided to aid focusing or defocusing such that any time differential delays can be reduced. Movement of the annular array in one, two or three-dimensions, or along any path, such as through use of probes and/or any conventional robotic arm mechanisms, may be implemented to scan and/or treat a volume or any corresponding space within ROI 12.

Figure 7D:
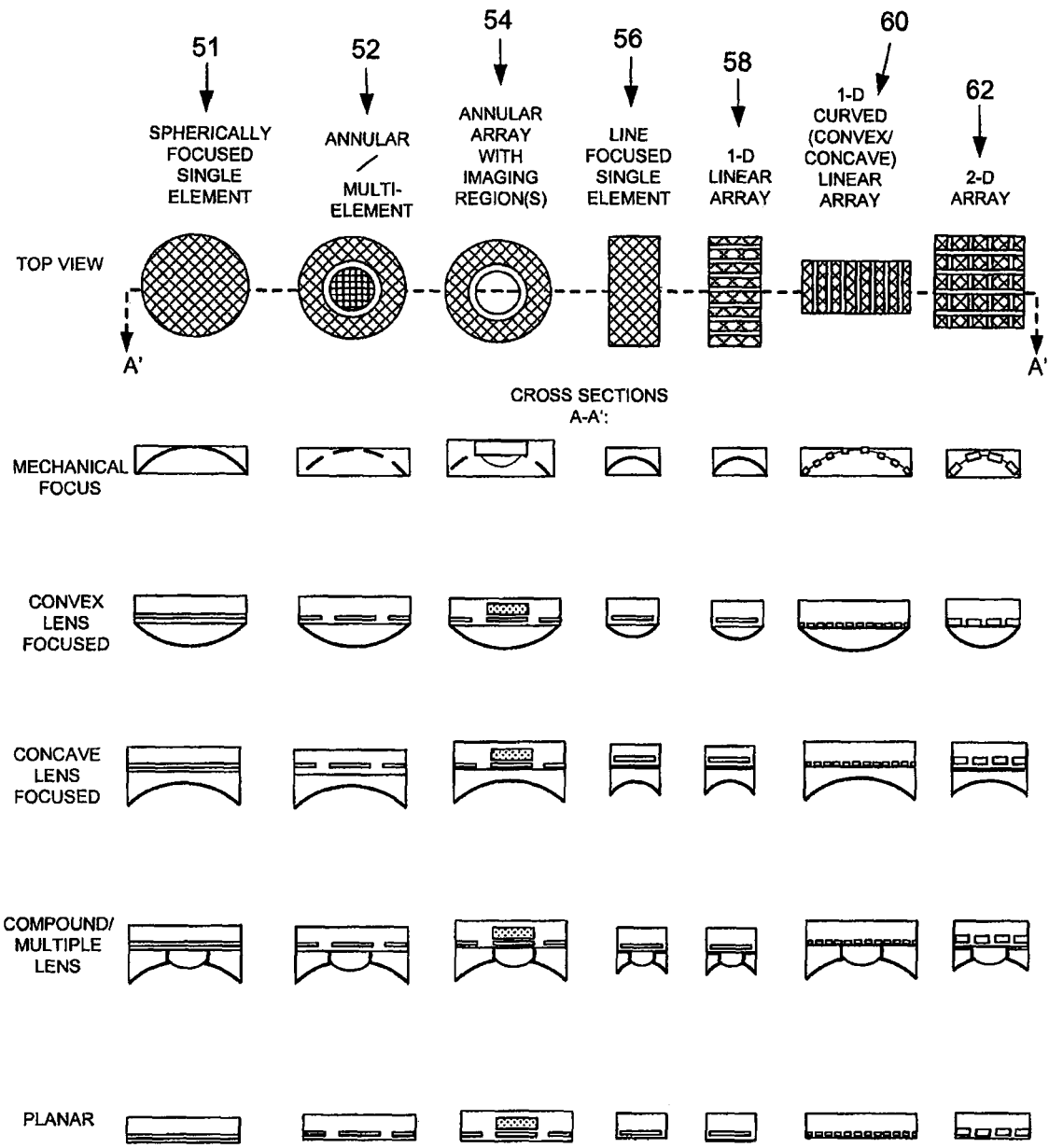

With reference to FIG. 7D, an exemplary transducer can also be configured as a spherically focused single element 51, an annular/multi-element 52, an annular element with imaging region(s) 54, a line-focused single element 56, a 1-D linear array 58, a 1-D curved (convex/concave) linear array 60, and/or 2-D array 62, with a mechanical focus, a convex lens focus, a concave lens focus, a compound/multiple lens focused, and/or planar array form to achieve focused, unfocused, or defocused sound fields for both imaging and/or therapy. Analogous to spherically focused single element 51 to be configured for multiple annuli 52 and/or imaging regions 54, an exemplary embodiment for the therapeutic line-focused single element 56, and 1-D and 2-D arrays 58, 60 and 62 is to dispose one or more imaging elements or imaging arrays in their aperture. In general a combination of imaging and therapy transducers or dual mode transducers can be used. In certain exemplary embodiments, spherical lens are used in treating acne and cylindrical lenses are used for treatment at ROI 12. Other lens shapes can still be used in other exemplary embodiments of the present invention.

Figure 8A:
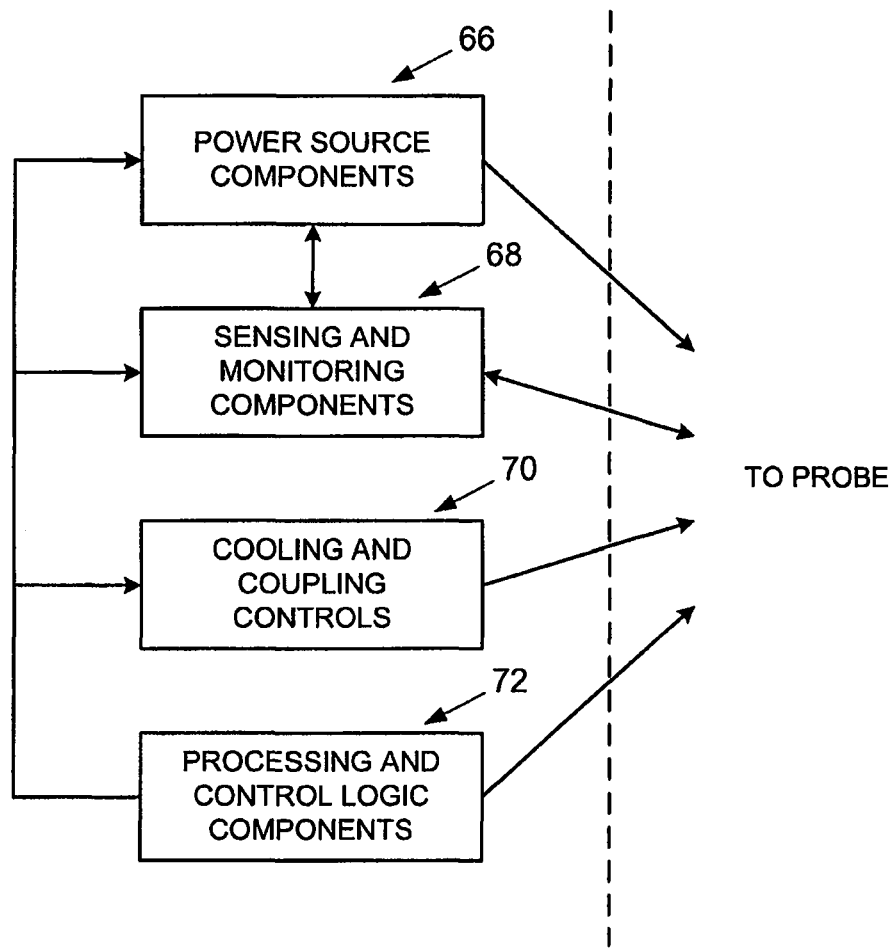
FIGS. 8A-8C illustrate block diagrams of an exemplary control system in accordance with exemplary embodiments of the present invention.
Figure 8B:
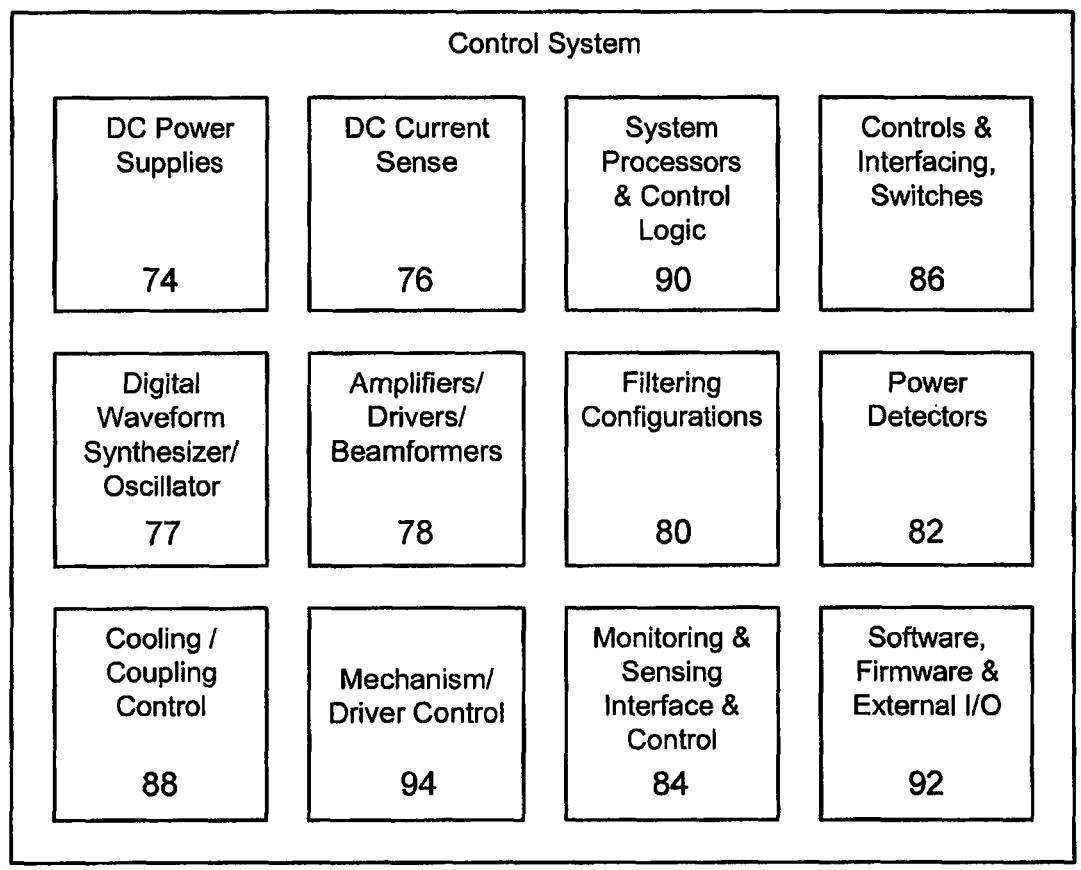
Figure 8C:
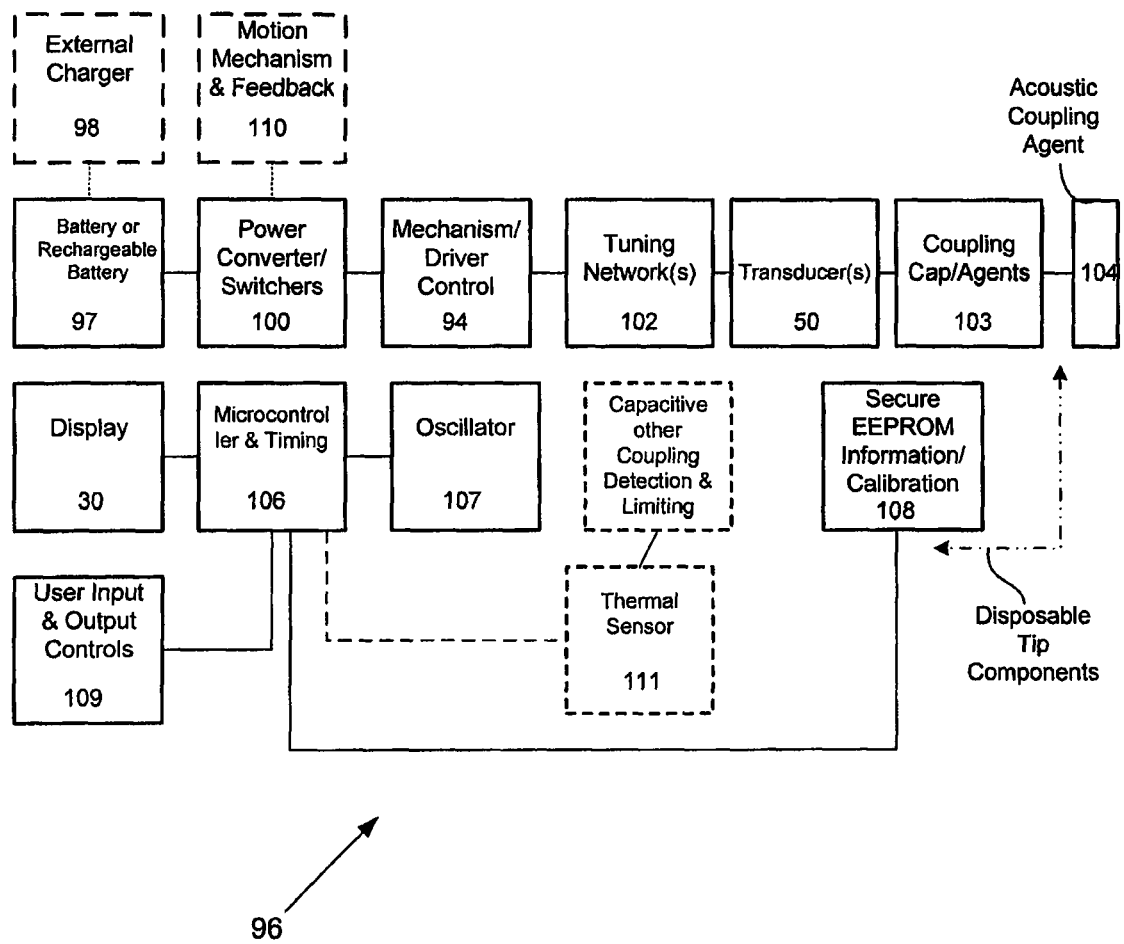

With reference now to FIGS. 8A-8C, an exemplary transducer is suitably controlled and operated in various manners by control system 28. Control system 28 may be in a hand-held format. Certain exemplary control systems 28 are disclosed in co-pending U.S. patent application Ser. No. 11/738,682 which is incorporated by reference above. Further, exemplary system 28 also comprises display 30. Exemplary displays 30 are also disclosed in co-pending U.S. patent application Ser. No. 11/738,682.

In an exemplary embodiment, an exemplary control system 28 is configured for coordination and control of the entire treatment process. For example, control system 28 can suitably comprise power source components 66, sensing and monitoring components 68, cooling and coupling controls 70, and/or processing and control logic components 72. Control system 28 can be configured and optimized in a variety of ways with more or less subsystems and components.

For example, control system 28 can comprise one or more direct current (DC) power supplies 74 configured to provide electrical energy for the entire control system, including power required by a transducer electronic amplifier/driver. A DC current sense device 76 can also be provided to confirm the level of power going into amplifiers/drivers for safety and monitoring purposes.

The amplifiers/drivers 78 can comprise multi-channel or single channel power amplifiers and/or drivers. In accordance with an exemplary embodiment for transducer array configurations, the amplifiers/drivers can also be configured with a beamformer to facilitate array focusing. An exemplary beamformer can be electrically excited by an oscillator/digitally controlled waveform synthesizer/oscillator 77 with related switching logic.

The power sourcing components can also include various filtering configurations 80. For example, switchable harmonic filters and/or matching may be used at the output of amplifier/driver/beamformer 78 to increase the drive efficiency and effectiveness. Power detection components 82 may also be included to confirm appropriate operation and calibration. For example, electric power and other energy detection components may be used to monitor the amount of power going to the probe.

Various sensing and monitoring components 84 may also be suitably implemented within the control system. For example, in accordance with an exemplary embodiment, the monitoring, sensing and interface control components 84 may be configured to operate with various motion detection systems implemented within the transducer to receive and process information such as acoustic or other spatial and/or temporal information from ROI 12. Sensing and monitoring components 84 can also include various controls, interfacing and switches 86 and/or power detectors. Such sensing and monitoring components can facilitate open-loop and/or closed-loop feedback systems within the system.

In an exemplary embodiment, the sensing and monitoring components comprise a sensor that is connected to an audio or visual alarm system to prevent overuse of the system. In this exemplary embodiment, the sensor senses the amount of energy transferred to the skin or the time that the system has be actively emitting energy. When a certain time or temperature threshold has been reached, the alarm sounds an audible alarm or causes a visual indicator to activate to alert the user that the threshold is reached. This prevents the user from overusing system. In an exemplary embodiment, the sensor could be operatively connected to the control system and force the control system to stop emitting ultrasound energy from the probe.

A cooling/coupling control system 88 may be provided to remove waste heat from an exemplary probe, provide a controlled temperature at the superficial tissue interface and deeper into tissue, and/or provide acoustic coupling from the probe to the ROI. Such cooling/coupling control systems can also be configured to operate in both open-loop and/or closed-loop feedback arrangements with various coupling and feedback components.

Additionally, an exemplary control system 28 can further comprise various system processor and digital control logic 90, such as one or more control or interfacing switches and associated components, including firmware and control software 92, which interfaces to user controls and interfacing circuits as well as input/output circuits and systems for communications, displays, interfacing, storage, documentation, and other useful functions. The system software controls all initialization, timing, level setting, monitoring, safety monitoring, and all other system functions required to accomplish user-defined treatment objectives. Further, various control switches can also be suitably configured to control operation. In an exemplary embodiment, control system 28 further comprises a mechanism and driver control 94.

With reference to FIG. 5C, an exemplary transducer is suitably controlled and operated in various manners by a hand-held format control system 96. An external battery charger 98 can be used with rechargeable-type batteries 97 or batteries can be single-use disposable types, such as AA-sized cells. Power converters 100 produce voltages suitable for powering a driver/feedback circuit with tuning network 102 driving a transducer coupled to the patient via one or more acoustic coupling caps 103. The cap can be composed of at least one of a solid media, semi-solid e.g. gelatinous media, and/or liquid media equivalent to an acoustic coupling agent (contained within a housing). Cap 103 is coupled to the patient with an acoustic coupling agent 104. Cap 103 and/or coupling agent 104 can be cooled, such as in a refrigerator, ice water, peltier cooling device, closed-loop cooling control or any other means of cooling. Cap 103 and/or coupling agent 104 can also be pre-heated, such as in an oven, hot water, resistive heating device, closed-loop heating or any other known means or mechanisms for heating.

In addition, a microcontroller and timing circuits 106 with associated software and algorithms provide control and user interfacing via display 30, oscillator 107, and other input/output controls 109 such as switches and audio devices. A storage element 108, such as an EEPROM, secure EEPROM, tamper-proof EEPROM, or similar device holds calibration and usage data. A motion mechanism with feedback 110 can be suitably controlled to scan the transducer, if desirable, in a line or two-dimensional pattern and/or with variable depth. Other feedback controls include a capacitive, acoustic, force, or other coupling detection means and/or limiting controls and thermal sensor 111. A combination of the secure EEPROM with at least one of coupling caps, transducer, thermal sensor, coupling detectors, or tuning network along with a plastic or other housing can comprise a disposable tip.

With reference again to FIG. 4, an exemplary system also comprises display 30 or a display system to provide images of ROI 12 in certain exemplary embodiments wherein ultrasound energy 16 is emitted from the transducer in a manner suitable for imaging. Display 30 can be any type of system that conveys images or information apart from images about the system 10 or ROI 12 to the user. Therefore, display 30 can be a computer monitor, television screen or it can simply be a simply type of indicator system such a liquid crystal display or light emitting diode display in various exemplary embodiments. Liquid crystal displays and light emitting diode displays are particularly useful when the system is a hand-held system.

Display 30 enables the user to facilitate localization of the treatment area and surrounding structures. After localization, delivery of ultrasound energy 16 at a depth, distribution, timing, and energy level to achieve the desired therapeutic effect is provided. Before, during, and/or after therapy, i.e., before, during and/or after delivery of ultrasound energy 16, monitoring of the treatment area and surrounding structures can be conducted to further plan and assess the results and/or providing feedback to the control system and a system operator via display 30.

In accordance with another exemplary embodiment of the present invention, an exemplary monitoring method may comprise monitoring the temperature profile or other tissue parameters of ROI 12 such as attenuation, speed of sound, or mechanical properties such as stiffness and strain of the treatment region and suitably adjust the spatial and/or temporal characteristics and energy levels of the ultrasound energy emitted from probe 26. The results of such monitoring techniques may be indicated on the display system by means of one-, two-, or three-dimensional images of monitoring results, or may simply comprise a success or fail-type indicator, or combinations thereof. Additional treatment monitoring techniques may be based on one or more of temperature, video, profilometry, and/or stiffness or strain gauges or any other suitable sensing technique.

In certain exemplary embodiments, system 10 is equipped with certain features to aid the user. One feature is a disposable tip that covers probe 26 during use. The disposable tip enables ultrasound energy 26 to pass through the tip and contact the patient. But, the disposable tip can be removed from probe 26 after use and replaced with a new disposable tip to prevent the spread of germs from one patient to another that might reside on the probe after contact with a patient's skin. Different size disposable tips can be used and fall within the scope of the present invention.

Present exemplary embodiments may be described herein in terms of various functional components and processing steps. It should be appreciated that such components and steps may be realized by any number of hardware components configured to perform the specified functions. For example, other exemplary embodiments may employ various medical treatment devices, visual imaging and display devices, input terminals and the like, which may carry out a variety of functions under the control of one or more control systems or other control devices. In addition, exemplary embodiments may be practiced in any number of medical contexts and that the exemplary embodiments relating to a system as described herein are merely indicative of exemplary applications for the disclosed subject matter. For example, the principles, features and methods discussed may be applied to any medical application. Further, various aspects of the present disclosure may be suitably applied to other applications, such as other medical or industrial applications.

The invention claimed is:

1. A treatment system comprising:
an ultrasound transducer configured to emit and focus a first beam of energy and a second beam of energy into a region of interest comprising a skin surface and subcutaneous tissue; and
an ultrasound controller coupled to the ultrasound transducer and configured for control of the ultrasound transducer;
the ultrasound transducer configured to direct the first beam of energy to and focus the first beam on the skin surface of the region of interest, the first beam of energy having a first temporal characteristic and a first spatial characteristic,
the ultrasound transducer configured to direct the second beam of energy to and focus the second beam on a location within the subcutaneous tissue in the region of interest, the second beam of energy having a second temporal characteristic and a second spatial characteristic,
the first beam of energy stimulating a first therapeutic effect at the skin surface,
the second beam of energy stimulating a second therapeutic effect in the subcutaneous tissue,
wherein the first spatial characteristic and the second spatial characteristic are different,
the first temporal characteristic and the second temporal characteristic are different, and
wherein the first therapeutic effect and the second therapeutic effect are different.

2. The treatment system according to claim 1, wherein the ultrasound transducer comprises an annular array.

3. The treatment system according to claim 1, wherein the first beam of energy has a frequency in a range of 0.15 to 10 MHz and the second beam of energy has a frequency in a range of 2 to 20 MHz.

4. The treatment system according to claim 1, wherein the ultrasound transducer is configured to simultaneously emit the first beam of energy and the second beam of energy.

5. The treatment system according to claim 1, wherein the first temporal characteristic is larger than the second temporal characteristic.

6. The treatment system according to claim 1, wherein the first therapeutic effect is ablative, and
wherein the second therapeutic effect is non-ablative.

7. The treatment system according to claim 1, wherein the first beam of energy is applied for a first time period to define the first temporal characteristic, and
wherein the second beam of energy is applied for a second time period to define the second temporal characteristic.

8. The treatment system according to claim 7, wherein the first time period is greater than the second time period.

9. The treatment system according to claim 1, wherein the first beam of energy has a first pattern, the second beam of energy has a second pattern, and
wherein the first pattern and the second pattern are different.

10. The treatment system according to claim 9, wherein the first pattern has a first width, and the second pattern has a second width, and
wherein the second width is greater than the first width.

\* \* \* \* \*